(12) United States Patent
Ward et al.

(10) Patent No.: US 7,196,231 B2
(45) Date of Patent: Mar. 27, 2007

(54) PROCESS FOR REMOVAL OF ACROLEIN FROM ACRYLONITRILE PRODUCT STREAMS

(75) Inventors: Gregory J. Ward, Gulf Breeze, FL (US); Bryan C. Blanchard, Milton, FL (US); Scott G. Moffatt, Pearland, TX (US); Valerie S. Monical, Houston, TX (US); Richard D. Murphy, Alvin, TX (US); Balshekar Ramchandran, Friendswood, TX (US)

(73) Assignee: Solutia, Inc., St. Louis, MO (US)

( * ) Notice: Subject to any disclaimer, the term of this patent is extended or adjusted under 35 U.S.C. 154(b) by 243 days.

(21) Appl. No.: 10/609,088

(22) Filed: Jun. 27, 2003

(65) Prior Publication Data

US 2004/0267054 A1 Dec. 30, 2004

(51) Int. Cl.
*C07C 43/32* (2006.01)
(52) U.S. Cl. .................................................... 568/594
(58) Field of Classification Search ................ 568/594
See application file for complete search history.

(56) References Cited

U.S. PATENT DOCUMENTS

| | | | |
|---|---|---|---|
| 3,185,636 A | 5/1965 | Stevens et al. ............... 202/57 |
| 3,328,266 A | 6/1967 | Modiano et al. ............... 203/34 |
| 3,459,639 A | 8/1969 | Borrel et al. .................. 203/37 |
| 3,462,477 A | 8/1969 | Caporali et al. ......... 260/465.3 |
| 4,625,059 A * | 11/1986 | Shibano et al. ............. 562/600 |
| 5,760,283 A | 6/1998 | Roof et al. .................. 558/463 |
| 6,074,532 A | 6/2000 | Patel et al. ..................... 203/6 |

FOREIGN PATENT DOCUMENTS

EP    01 10 861    11/1983

* cited by examiner

*Primary Examiner*—Joseph K. McKane
*Assistant Examiner*—Yong Chu
(74) *Attorney, Agent, or Firm*—Jones, Tullar & Cooper, P.C.; John P. Foryt

(57) ABSTRACT

Acrolein is removed from a process stream such as a process stream generated in the manufacture of acrylonitrile. The process includes reacting the acrolein with a compound containing a reactable thiol or hydroxyl moiety in the presence of an acid catalyst. The present process provides for a refined process stream that contains no more than 5 ppm by weight unreacted acrolein.

16 Claims, No Drawings

PROCESS FOR REMOVAL OF ACROLEIN FROM ACRYLONITRILE PRODUCT STREAMS

BACKGROUND OF THE INVENTION

This invention relates to the purification of acrylonitrile. More particularly, it relates to removal of acrolein from acrolein-containing acrylonitrile process streams by reaction of the acrolein with a scavenger compound to produce an acrolein derivative.

Acrylonitrile is a well-known article of commerce widely used in the manufacture of synthetic resins and fibers and as a valuable intermediate in the synthesis of many organic compounds. In most large-scale industrial processes for producing this nitrile, minor amounts of undesired byproducts and contaminants, including acetone, acrolein, acetaldehyde, and other similar carbonyl compounds, are simultaneously produced.

In most commercial applications utilizing acrylonitrile as a starting material, it is critical that the starting material be in as pure a state as possible as even minute traces of impurities can cause extremely low production yields and/or inferior end product quality. This impact is particularly prevalent when acrylonitrile is used in the preparation of synthetic resins and fibers.

The presence of even very small trace quantities of acrolein renders the acrylonitrile unsuitable for many applications. For example, acrolein can act as a crosslinker or an alkylol adduct with acrylamide when the nitrile is converted to acrylamide and then polymerized, such as for eventual end-use as a fiber or flocculent. The presence of acrolein contaminant can thereby result in polyacrylamide that is of insufficient molecular weight or which contains undesirable insoluble material. Thus, it is essential for many end uses that acrolein concentrations in acrylonitrile starting materials, if any, be reduced to below 15 ppm, more preferably 5 ppm or less, by weight of the commercial grade acrylonitrile if it is to be successfully marketed.

Although prior art commercial acrylonitrile production systems typically include purification steps often using distillation processes, acrolein reduction to this required level is difficult. More specifically, prior art methods for removal of acrolein from the crude acrylonitrile stream have typically involved pH adjustments and/or control at various points in the process which add cost or have undesirable impact such as side reaction catalysis and equipment fouling. In U.S. Pat. No. 3,185,636 to Stevens et al, the absorber column pH is maintained at a substantially neutral or slightly alkaline pH, whereby the saturated carbonyl compounds in the reactor effluent combine with the excess hydrogen cyanide to form the corresponding cyanohydrin. In U.S. Pat. No. 3,462,477 to Caporali et al a pH of between 7.5 and 11 was required to separate the acrolein from the crude acrylonitrile by distillation. In published EP application 0110861, acrolein is removed by maintaining the pH in the zone of maximum acrolein concentration of the recovery column at from about 5.25 to 7.

Other attempts to separate acrolein and other byproducts from acrylonitrile have not successfully reduced the acrolein content to the required level. In U.S. Pat. No. 3,328,266 to Modiano et al the crude acrylonitrile stream from the absorber with a pH generally between 9 and 9.5 is subjected to extractive distillation apparently without any further adjustment of pH. The acrolein content remains high, however, even after the third stage of the distillation is completed and does not produce acrylonitrile of sufficient purity for fiber production.

The separation of acrylonitrile from acetonitrile and small quantities of acrolein is discussed in U.S. Pat. No. 3,459,639 to Borrel et al. Under the disclosed conditions for the distillation recovery column, the acrolein was not significantly affected and remained above 200 parts per million in the separated organic product phase.

Yet other prior art acrolein removal processes utilize additives to improve and increase acrolein reduction. For example, U.S. Pat. No. 5,760,283 describes the addition of strong bases in the recovery section of the process while U.S. Pat. No. 6,074,532 describes adding a substituted aromatic amine prior to distillation. These types of processes add significant cost to the overall process and have the potential to catalyze unwanted side reactions and to form undesirable byproducts.

Japanese application no. 53-60040 describes the removal of acrolein with an ion exchange resin. Accordingly, there continues to be an unmet need for an inexpensive and effective process for removal of acrolein from process streams that achieves the purity levels critical for use of these process streams.

SUMMARY OF THE INVENTION

This invention provides a process for the removal of sufficient amounts of acrolein from acrolein-containing process streams to result in reduction of the acrolein content to less than about 15 and preferably less than 5 parts per million.

An object of the present invention is, therefore, to provide an inexpensive process for removing acrolein from an unrefined acrolein-containing process stream.

Another object of the present invention is to provide a process for removing acrolein from an unrefined acrolein-containing process stream that reduces acrolein levels to below the level critical for commercial use, preferably in conjunction with acrylonitrile-containing process streams usable in polymerization processes.

Another object of the present invention is to provide a process for removing acrolein from an unrefined acrolein-containing process stream without generating unwanted by-products or contaminants as part of the process.

The invention achieves these and other desirable objectives by providing a process for removal of acrolein from an acrolein-containing process stream that includes reacting the acrolein in the presence of an acid catalyst with a scavenger compound that contains a reactable thiol or hydroxyl moiety to form an acrolein derivative. The acrolein content in the refined process stream can be effectively reduced to less than about 5 parts per million.

DESCRIPTION OF THE PREFERRED EMBODIMENTS

The present invention is directed to a process for separating acrolein from an acrolein-containing process stream. In a first preferred embodiment, the acrolein-containing process stream further includes acrylonitrile and more preferably is a unrefined acrolein-containing process stream further including acrylonitrile, cyanide compounds, and potentially other byproducts and contaminants that are generated as part of an acrylonitrile manufacturing process. The specific composition of the preferred process stream will depend on a number of factors, including but not limited to the acrylonitrile reaction chemistry utilized in the acrylonitrile generating process and the specific step in the formation process at which the stream is generated. Most preferably, the process stream is generated as part of a process for manufacture of acrylonitrile by the catalytic ammoxidation of propylene. To the extent the unrefined process stream contains cyanide compounds, it is particularly preferred that they be substantially removed from the stream prior to the reaction step discussed in detail below wherein a scavenger compound reacts with the acrolein in the stream such that the reaction step is performed in the substantial absence of a cyanide compound.

In a second embodiment, the acrolein-containing process stream further includes acrylic acid and more specifically is an acrolein-containing process stream further including acrylic acid, and potentially other byproducts and contaminants that are generated as part of an acrylic acid manufacturing process.

The process of the present invention includes reacting acrolein that is present in the acrolein-containing process stream with a scavenger compound that contains a reactable thiol or hydroxyl moiety to form an acrolein derivative. In a first preferred embodiment, the process includes reacting acrolein that is present in the acrolein-containing process stream with a scavenger compound that contains a reactable thiol moiety. A thiol moiety is defined herein as the moiety —SH. Any chemical compound containing a thiol moiety that is sufficiently soluble to facilitate reaction thereof with the acrolein (preferably a compound characterized by a solubility of at least 1% by weight in the process stream) in the acrolein-containing process stream is useful in the process of the present invention, including mercaptoacetic acid, 2-mercapto ethanol, 2-aminoethanethiol and ethylene glycol bisthioglycolate. A particularly preferred compound is mercaptoacetic acid. In this preferred embodiment, the acrolein derivative formed by the process of the present invention is an acrolein thioacetal.

In a second embodiment, the process of the present invention includes reacting acrolein that is present in the acrolein-containing process stream with a scavenger compound that contains a reactable hydroxyl moiety. A hydroxyl moiety is defined herein as the moiety —OH. Any chemical compound containing a reactable hydroxyl moiety that is sufficiently soluble to facilitate reaction thereof with the acrolein (preferably a compound characterized by a solubility of at least 1% by weight in the process stream) in the acrolein-containing process stream is suitable for the process of the present invention, including but not limited to alcohols, diols, glycerol, polyols, phenols, hydroxy acids, hydroxy nitrites, hydroxy esters and the like. A preferred compound is lactic acid. In this embodiment, the acrolein derivative formed by the process of the present invention is an acrolein acetal. In this embodiment, it is preferable that the acrolein-containing process stream includes water, more preferably a water content of about 2% to about 3% by weight at commencement of the reaction step. Even more preferably, the water content of the process stream is reduced during the reaction step to no more than about 0.5% by weight water. Accordingly, in this embodiment the process preferably further includes reducing the water content of the process stream to no more than 0.5% water by weight.

The reaction step in the process of the present invention is performed preferably at a pH of between about 3.0 and about 7.0, preferably in the presence of an acid catalyst. The acid catalyst may be a liquid or a solid acid catalyst. Examples of the former are glycolic acid and acetic acid. Examples of solid acid catalysts include polymer based catalysts and ion exchange resins such as functionalized styrene divinylbenzene copolymers with sulfuric acid type functional groups. Suitable catalysts are sold under the AMBERLYST® trademark by Rohm and Haas.

In a first preferred embodiment, the acid catalyst is already present in the acrolein-containing process stream, such that the process stream includes an acid catalyst. For example, in the embodiment wherein the acrolein-containing process stream further contains acrylonitrile and is a stream that is part of an acrylonitrile manufacturing process, the acid environment may be created by the presence of acid added in an upstream hydrogen cyanide purification column to inhibit hydrogen cyanide polymerization. In a second embodiment, the acid environment is created by the presence of an added acid catalyst and the process of the present invention further includes adding an acid catalyst to the process stream prior to the reaction step. Preferred acid catalyst for this embodiment includes glycolic acid and acetic acid, with acetic acid being particularly preferred. It is also particularly preferred to select a scavenger compound that is an acid to further establish the acidic environment for the reaction.

The reaction of the acrolein with the scavenger forms, in addition to the acrolein derivative, a refined process stream containing the acrolein derivative. Preferably, the refined process stream includes no more than 5 ppm unreacted acrolein.

Preferably, the process of the present invention further includes separating the acrolein derivative from the refined process stream. Suitable methods for this removal step will be readily apparent to one of ordinary skill in the art and will be selected based on many factors, including, for example, the chemical structure of the acrolein derivative (e.g., acrolein acetal or acrolein thioacetal). Suitable separation methods include distillation, with utilization of existing equipment present in the overall manufacturing process being particularly preferred The following examples, while not intended to limit in any way the scope of the process of the present invention, are set forth to further illustrate its various embodiments and demonstrate its usefulness.

EXAMPLE 1

To demonstrate the utility of scavenger compounds containing hydroxyl moieties in the process of the present invention, a solution containing 95 wt % acrylonitrile, 5 wt. % acetic acid, 155 ppm (wt) acrolein and 500 ppm (wt) phenothiazine as a non-phenolic polymerization inhibitor was made. The acrylonitrile that was used was first distilled to remove most of the water and hydroquinone mono methyl ether inhibitor. The water concentration of the acrylonitrile for each of these tests was 0.3 wt %. The acrolein was also flash distilled to remove the hydroquinone mono methyl ether inhibitor prior to use.

0.1 g of each of the hydrozyl-containing scavenger compounds listed in Table 1 below was then added to separate 10 gram samples of the above solution and the resulting mixtures were placed in an oven at 50° C. for the period of time indicated in Table 1. The results of the test are detailed in Table 1 below:

TABLE 1

| ACR Scavenger | Acrolein Initial | Time Hrs. | Acrolein at Time | Acrolein % Change | Time Hrs. | Acrolein at Time | Acrolein % Change |
|---|---|---|---|---|---|---|---|
| Ethanol | 155 | 24 | 130 | −16.13 | 96 | 119 | −23.23 |
| Butanol | 155 | 24 | 146 | −5.81 | 96 | 116 | −25.16 |
| Ethylene glycol | 155 | 24 | 143 | −7.74 | 96 | 110 | −29.03 |
| Propylene glycol | 155 | 24 | 145 | −6.45 | 96 | 116 | −25.16 |
| Diethylene glycol | 155 | 24 | 153 | −1.29 | 96 | 132 | −14.84 |
| Glycerin | 155 | 24 | 152 | −1.94 | 96 | 114 | −26.45 |
| Glycolic acid | 155 | 24 | 146 | −5.81 | 96 | 120 | −22.58 |
| Lactic acid | 155 | 24 | 129 | −16.77 | 96 | 110 | −29.03 |

As demonstrated by the results above, the process of the present invention can remove essentially all of the acrolein from acrolein-containing process streams. The remaining acrolein can then be removed by existing refining trains such that the final concentration is less than 5 ppm and possibly as low as 1 ppm. It is recognized that, in view of these results, the extent of the acrolein removal achieved when a scavenger compound containing a hydroxy 1 moiety is utilized in the process of the present invention may not be sufficient for some end-use applications of the refined process stream.

EXAMPLE 2

To demonstrate the utility of scavenger compounds containing thiol groups in the process of the present invention, a solution containing 99.7 wt % acrylonitrile, 0.2 wt. % acetic acid, 1067 ppm (wt) acrolein was made. No polymerization inhibitor was added. The acrylonitrile that was used was first distilled to remove most of the water and hydroquinone mono methyl ether inhibitor. The water concentration of the acrylonitrile in these tests was 0.4 wt %. The acrolein was also flash distilled to remove the hydroquinone mono methyl ether inhibitor prior to use.

0.025 grams of each of the thiol-containing scavenger compounds listed in Table 2 below was added to separate 10 gram samples of the above solution. The resulting mixture was placed in an oven at 65° C. for the period of time indicated in Table 2. The results of the test are detailed in Table 2 below:

TABLE 2

| Acrolein Scavenger | Acrolein Initial | Time Hrs. | Acrolein at Time | Acrolein % Chance |
|---|---|---|---|---|
| 1,2-Ethanedithiol | 1067 | 24 | 322 | −69.82 |
| Mercaptoacetic acid | 1067 | 24 | 9 | −99.16 |
| 2-mercaptoethanol | 1067 | 24 | 59 | −94.47 |
| 2-aminoethanethiol | 1067 | 24 | 8 | −99.25 |
| Ethylene glycol bisthiglycolate | 1067 | 24 | 48 | −95.50 |

As demonstrated by the results above, the process of the present invention effectively removes acrolein from acrolein-containing process streams. Notably, preferred scavenger compounds containing thiol groups achieve acrolein removal that is necessary for the most critical end use applications for the refined process stream.

EXAMPLE 3

To further demonstrate the utility of scavenger compounds containing thiol groups in the process of the present invention as well as the impact of scavenger solubility in the unrefined process stream on the result, a solution containing 99.6 wt % deionized water, 0.2 wt. % acetic acid, 1000 ppm (wt) acrolein was made. 0.04 grams of each of the thiol-containing scavenger compounds listed in Table 3 below was added to separate 10 gram samples of the above solution. The resulting mixture was placed in an oven at 65° C. for the period of time indicated in Table 3. The results of the test are detailed in Table 3 below:

TABLE 3

| Acrolein Scavenger | Acrolein Initial | Time Mins. | Acrlein at Time | Acrolein % Change |
|---|---|---|---|---|
| 1,2-Ethanedithiol* | 1000 | 30 | 0 | −100 |
| Mercaptoacetic acid | 1000 | 30 | 0 | −100 |
| Ethylene glycol Bisthiglycolate* | 1000 | 30 | 0 | −100 |

*denotes formation of precipitate

As demonstrated by the results above, the process of the present invention effectively removes acrolein from acrolein-containing process streams. Notably, mercaptoacetic acid demonstrated particularly desirable solubility in the subject acrolein-containing process stream by producing an acrolein reaction product that remained in solution and did not precipitate, While the present invention has been described and exemplified in detail herein, it is to be understood that various modifications and variations thereto may be made without departing from its spirit and scope.

What is claimed is:

1. A method for removing acrolein from a process stream comprising
   (a) providing a process stream comprising acrolein; and
   (b) reacting said acrolein in the presence of an acid catalyst with a scavenger compound containing a reactable hydroxyl moiety selected from the group consisting of alcohols, diols, glycerol, polyols, phenols, hydroxyl acids, hydroxyl nitriles and hydroxyl esters having a solubility of at least 1% in the process stream to form an acrolein derivative in a refined process stream.

2. The method of claim 1 wherein said acid catalyst is a solid acid catalyst.

3. The method of claim 1 wherein said process stream further comprises said acid catalyst.

4. The method of claim 1 further comprising adding said acid catalyst to said process stream prior to said reaction step (b).

5. The method of claim 1 wherein said reaction step (b) is conducted at a pH of between 3.0 and 7.0.

6. The method of claim 4 wherein said acid catalyst is selected from the group consisting of glycolic acid and acetic acid.

7. The method claim 1 wherein said process stream further comprises water.

8. The method of claim 7 wherein said process stream includes 2.0% to 3.0% by weight water at commencement of said reaction step (b).

9. The method of claim 8 further comprising the step of reducing the water content of said process stream to no more than 0.5% water.

10. The method of claim 1 wherein said acrolein derivative is an acrolein acetal.

11. The method of claim 1 further comprising separating said acrolein derivative from said refined process stream.

12. The method of claim 11 comprising distillation of said refined process stream.

13. The method of claim 1 wherein said process stream further comprises acrylontirile.

14. The method of claim 1 wherein said reacting step is performed in the substantial absence of a cyanide compound.

15. The method of claim 1 wherein said process stream further comprises acrylic acid.

16. A method for removing acrolein from a process stream comprising (a) providing a process stream comprising acrolein; and (b) reacting said acrolein with a scavenger compound containing a reactable hydroxyl moiety selected from the group consisting of alcohols, diols, glycerol, polyols, phenols, hydroxyl acids, hydroxyl nitriles and hydroxyl esters having a solubility of at least 1% in the process stream at a pH of between 3.0 and 7.0 to form an acrolein derivative in a refined process stream.

* * * * *